United States Patent
Vicari et al.

(10) Patent No.: US 7,282,614 B2
(45) Date of Patent: Oct. 16, 2007

(54) METHOD FOR THE PRODUCTION OF PROPARGYL ALCOHOL

(75) Inventors: Maximilian Vicari, Limburgerhof (DE); Martin Rudloff, Goennheim (DE); Andreas Kramer, Friedelsheim (DE); Ronald Drews, Birkenau (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/565,186

(22) PCT Filed: Jul. 3, 2004

(86) PCT No.: PCT/EP2004/007269

§ 371 (c)(1),
(2), (4) Date: Jun. 28, 2006

(87) PCT Pub. No.: WO2005/019144

PCT Pub. Date: Mar. 3, 2005

(65) Prior Publication Data

US 2007/0112226 A1    May 17, 2007

(30) Foreign Application Priority Data

Jul. 24, 2003    (DE) .............................. 103 33 598

(51) Int. Cl.
*C07C 33/042*    (2006.01)

(52) U.S. Cl. ..................................... 568/874; 568/873

(58) Field of Classification Search ................ 568/873, 568/874

See application file for complete search history.

(56) References Cited

U.S. PATENT DOCUMENTS 3,087,970 A    4/1963    Moore et al.
4,117,248 A    9/1978    Prater et al.

FOREIGN PATENT DOCUMENTS

| CH | 220204 | 6/1942 |
|---|---|---|
| DE | 726714 | 10/1942 |
| DE | 740514 | 11/1943 |
| DE | 1013279 | 8/1957 |
| DE | 1072985 | 1/1960 |
| DE | 1075593 | 2/1960 |
| DE | 12 84 964 | 12/1968 |
| DE | 24 21 407 | 10/1975 |
| FR | 1144265 | 10/1957 |
| GB | 784638 | 10/1957 |
| GB | 805861 | 12/1958 |

*Primary Examiner*—Elvis O. Price
(74) *Attorney, Agent, or Firm*—Oblon, Spivak, McClelland, Maier & Neustadt, P.C.

(57) ABSTRACT

The present invention provides a process for preparing propargyl alcohol by converting an aqueous formaldehyde solution comprising acetylene over a catalyst comprising copper acetylide at an operating pressure of from 1 to 15 bar and from 70 to 120° C. without forming a continuous gas phase, in which the aqueous formaldehyde solution comprises an organic solvent for acetylene and the catalyst is arranged in a fluidized bed.

8 Claims, 1 Drawing Sheet

METHOD FOR THE PRODUCTION OF PROPARGYL ALCOHOL

Figure 1:
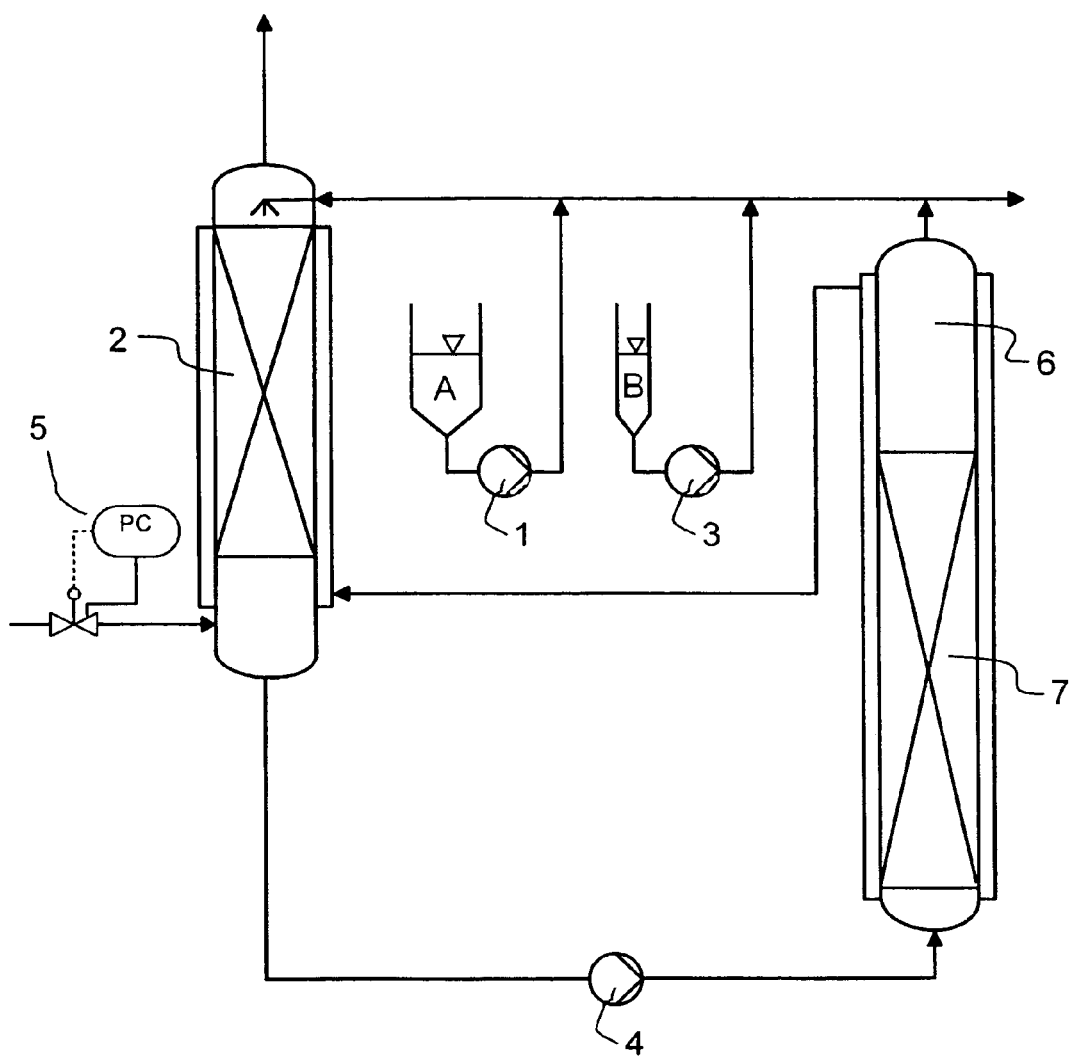

The invention relates to a process for preparing propargyl alcohol by converting an aqueous formaldehyde solution comprising acetylene in the presence of a catalyst comprising copper acetylide at an operating pressure of from 1 to 15 bar and from 70 to 120° C. without forming a continuous gas phase, in which the aqueous formaldehyde solution comprises an organic solvent for acetylene and the catalyst is arranged in a fluidized bed.

The ethynylation for preparing alkynols is a process which has been known for some time. Its main disadvantage is the danger of gaseous acetylene, which is known to force expensive safety measures to be taken, for example designing the apparatus for more than ten times the operating pressure.

In order to operate the process in a very safe and economically viable manner, DE-A 24 21 407 therefore proposes the occurrence of a free continuous gas phase only in the plant parts for acetylene compression. However, the synthesis reactors are operated only with acetylene dissolved in formaldehyde solution. According to DE-A 24 21 407 mainly 1,4-butyinediol is formed under these conditions.

DE-A 1 284 964 discloses a process for preparing propargyl alcohol over a fixed bed catalyst, in which a solvent may optionally be added. When carrying out reactions in fixed bed reactors, very large reactor volumes and/or very long reaction times generally have to be accepted, since the productivity of fixed bed catalysts is relatively low. In addition, the exchange of used catalysts is associated with considerable cost and in-convenience and entails long downtimes.

In order to utilize the activity of the catalysts in the best possible manner, small catalyst particles extending down to powders are also used and are suspended in the reaction medium. However, the removal of the catalyst from the reaction medium here entails high technical complexity.

For instance, U.S. Pat. No. 4,117,248 discloses that the reaction of formaldehyde and acetylene in suspension is advantageous. However, a disadvantage of this method is that a continuous acetylene gas phase occurs and that only 0.7% by weight of propynol is formed, which cannot be removed from the reaction mixture in an economically viable manner.

U.S. Pat. No. 3,078,970 also discloses a process, which is free of a continuous acetylene gas phase, for preparing propargyl alcohol using N-alkylpyrrolidone in suspension. A disadvantage is again in particular the finely divided catalyst in suspension, which makes necessary a complicated and troublesome removal, for example by filtration or centrifugation.

However, the economic viability of a heterogeneously catalyzed ethynylation process depends decisively upon the productivity of the catalyst, its ease of removal from the reaction medium and a high plant availability.

It is an object of the present invention to provide a process for preparing propargyl alcohol which enables the simple and safe preparation by ethynylation and avoids the disadvantages of the prior art processes. It is a particular desire that a high space-time yield be enabled with simple catalyst removal.

We have found that this object is achieved by a process for preparing propargyl alcohol by converting an aqueous formaldehyde solution comprising acetylene over a catalyst comprising copper acetylide at an operating pressure of from 1 to 15 bar and from 70 to 120° C. without forming a continuous gas phase, wherein the aqueous formaldehyde solution comprises an organic solvent for acetylene and the catalyst is arranged in a fluidized bed.

According to the invention, the catalyst particles are preferably fluidized in a certain manner by the flow-through of reaction medium.

In the preferred embodiment of the invention, the fluidization is carried out in such a way that the formation of an expanded liquid-solid fluidized bed is achieved. This is accompanied by a distinct expansion of the catalyst bed, a corresponding increase in the free volume between the catalyst particles and distinct backmixing of the catalyst particles.

In another embodiment, the fluidization is carried out in such a way that the expansion of the catalyst bed and the increase in the free volume between the catalyst particles remain low. This results in the catalyst particles obtaining a certain mobility. However, no macroscopic mixing of the catalyst bed should occur. This is achieved by fluidization of the catalyst bed at the fluidization point. In a fluidized bed beyond the fluidization point, for instance in an expanded fluidized bed, there is macroscopic mixing.

In both embodiments, the fluidization of the catalyst is carried out in such a way that no significant amounts of catalyst are discharged from the ethynylation reactor. This behavior is achieved by suitably selected flow through the catalyst bed. The optimum flow-through, expressed, for example, by the superficial velocity, has to be adapted to the desired embodiment of the invention (expanded fluidized bed or fluidized bed at the fluidization point), the viscosity and density of the reaction medium and the properties of the catalyst particles, in particular their size, shape, density and porosity.

Too low a superficial velocity leads to a loss of fluidization. The achievement of the superficial velocity necessary for the minimum fluidization achieves lasting dissolution and formation of solid contacts, which is characteristic of a fluidized bed at the fluidization point. An increase in the superficial velocity leads to an increase in the separation between the particles and to a higher mobility of the particles and therefore to macroscopic mixing of the catalyst bed (expanded fluidized bed). Excessively high superficial velocities eventually lead to massive discharge of catalyst particles out of the reactor with the reaction medium.

The optimum parameters for the process according to the invention at the fluidization point may be determined theoretically or experimentally. A suitable experimental process for finding the desired fluidization point is the analysis of the pressure drop over the catalyst bed as a function of the superficial velocity. When the superficial velocities are too low, the pressure drop rises continuously with the flow rate, corresponding to the conditions in a fixed bed; the bed is not yet in the fluidized state. In contrast, above the fluidization rate sought (minimum fluidization rate), the rise in the pressure drop is distinctly smaller or remains constant.

A measure of the presence of a fluidized bed at the fluidization point or expanded fluidized bed is the expansion factor of the catalyst bed, i.e. the ratio of the volume taken up by the fluidized catalyst bed to the volume of the catalyst bed without flow-through.

In the case of a fluidized bed at the fluidization point, that factor is $\leq 1.15$; preferably <1.10 and more preferably <1.05. The volume of the reaction zone filled by catalyst particles during the flow-through with reaction medium is thus greater by max. 15%, preferably max. 10%, particularly max. 5%, than the state without flow-through.

Suitable operating points for the process according to the invention with the formation of an expanded fluidized bed are at superficial velocities distinctly beyond fluidization point. These operating points lead to expansion factors of from 1.01 to 4; preferably from 1.05 to 2 and more preferably from 1.1 to 1.5 (ratio of the volume taken up by the fluidized catalyst bed to the volume of the catalyst bed without flow-through). The volume of the reaction zone filled by catalyst particles during flow-through with reaction medium is thus greater by from 1 to 300%, preferably from 5 to 100%, more preferably from 10 to 50%, than the state without flow-through.

The process according to the invention is carried out with a copper acetylide catalyst which is suitable for ethynylation according to Reppe. These are described, for example, in DE-A 1 072 985, DE-A 1 075 593, CH-B 220 204, GB-B 784 638, FR-B 1 144 265, DE-B 726 714, DE-B 740 514, DE-B 1 013 279 and GB-B 805 861.

The catalyst may be introduced into the ethynylation reaction in powder form or preferably as shaped bodies. Shaped bodies may be prepared from pulverulent raw materials by methods known to those skilled in the art, for example tableting, agglomeration or extrusion, as described, inter alia, in Handbook of Heterogenous Catalysis, Vol. 1, VCH Verlagsgesellschaft Weinheim, 1997, p. 414-417. In the shaping, assistants known to those skilled in the art, such as binders, lubricants and/or solvents, may be added. The catalyst may be used for the polymerization, for example, in the form of cylinders, extrudates, ribbed extrudates, spheres, rings or spall. Preference is given to using spheres, sphere like shaped bodies or spall.

The particle size of the catalyst may be varied within wide limits depending on the reaction conditions and catalyst type. Typically, the individual catalyst particles for the fluidized bed method according to the invention have a size of from 0.2 to 3 mm, preferably from 0.8 to 1.5 mm.

The ethynylation is generally carried out at temperatures of from 70 to 120° C., preferably from 80 to 90° C., and an operating pressure in the reaction chamber, in particular in the ethynylation reactor, of from 1 to 15 bar, preferably from 3 to 7 bar. In the context of the invention, continuous gas phase refers to gas spaces within the reaction chamber which go beyond individual, discrete bubbles.

In the process according to the invention, an organic solvent for acetylene, said solvent being miscible with aqueous formaldehyde, is added to the aqueous formaldehyde solution in which acetylene is present in dissolved form. The concentration of formaldehyde in the solution is advantageously from 1 to 40% by weight, in particular from 10 to 30% by weight, based on the overall mixture. Preferred organic solvents for acetylene are those which, under the reaction conditions, absorb more than 2 $cm^3$ of gaseous acetylene per cubic centimeter of solvent. Suitable solvents are therefore cyclic ethers such as tetrahydrofuran, dimethyltetrahydrofuran, hexamethylene oxide or dioxane, and also lactones such as butyrolactone, and disubstituted carboxamides such as N-methylpyrrolidone and dimethylformamide, and also acetals such as formaldehyde dimethyl acetal, and alcohols such as methanol. Particular preference is given to using tetrahydrofuran as the solvent.

The weight ratio of organic solvent to formaldehyde in the aqueous formaldehyde solution is from 0.1:1 to 20:1, preferably from 1.5:1 to 4:1.

The reaction according to the invention proceeds in the liquid phase with acetylene which is dissolved in a formaldehyde solution containing aqueous organic solvent and is fed in this form to the reaction chamber, i.e. the ethynylation reactor, and the partial pressure of the acetylene in the aqueous formaldehyde solution comprising an organic solvent is from 0.1 to 95% of the operating pressure in the reaction chamber.

The formaldehyde solution which is to be converted and comprises aqueous, organic solvent is admixed with acetylene before entry into the reaction chamber, for example the ethynylation reactor, and the amount of acetylene may be, for example, from 0.1 to 1 time the particular saturation concentration. The solution to be converted in this case also includes the recycled liquid in the case of a continuous method, which still contains formaldehyde but is depleted in acetylene.

Acetylene is mixed with the aqueous formaldehyde solution which comprises organic solvent in a suitable catalyst-free preliminary chamber of the reaction vessel or preferably in a suitable mixing nozzle arrangement or preferably in a separate gas/liquid contact apparatus, for example a reaction tube which serves as a saturator and is optionally filled with packings, for example random packings.

The pH of the formaldehyde solution which is saturated with acetylene and comprises aqueous organic solvent is adjusted by metering in a from 1 to 5% by weight sodium bicarbonate solution to from 3 to 8, preferably from 6 to 7. However, the pH may also be adjusted using sodium carbonate solution or sodium hydroxide solution.

Advantageously, the process may be carried out in an apparatus which is described by the figure described below.

The aqueous formaldehyde solution (A) comprising tetrahydrofuran is conducted through the conveying pump (1) into the upper section of the reaction tube (2) which serves as a saturator and is provided with a packing, for example random packing. Optionally, the formaldehyde solution may be mixed with reaction effluent from the ethynylation. The compressor which is not shown is used to feed acetylene from below under a pressure of generally from 4 to 6 bar into the reaction tube (2) serving as a saturator, in which a certain pressure of from 3 to 4 bar and a temperature of from 70 to 85° C. are maintained. The conveying pump (3) is used to meter in sufficient from 1 to 5% by weight sodium bicarbonate solution (B) that the pH of the acetylene-saturated, aqueous formaldehyde solution which leaves the saturator (2) via pipeline (4) by means of a pump (5) and comprises organic solvent preferably has a pH of from 6 to 7.

A pressure regulator (5) regulates the plant pressure via the acetylene feed. A small amount of acetylene is decompressed under mass flow control at the top of the saturator and is lost as offgas. This offgas may in principle, after appropriate enrichment with acetylene and removal of the carbon dioxide, be fed back to the acetylene feed. The use mixture is pumped from the bottom of the saturator (2) by means of a pump (5) into the ethynylation reactor (6). In the ethynylation reactor (6), the copper acetylide catalyst in the form of 1.5 mm spall (7) is kept fluidized in the reactor by appropriate amounts of liquid pumped by circulation (circulation rate). The circulation rate is set in such a way that there is a constant expansion of preferably x. The reaction proceeds substantially isothermally, since the heat of reaction produced is passed through the reactor wall to the oil present in the jacket of the reactor.

At the top of the ethynylation reactor, the effluent is decompressed, controlled by the liquid phase level of the saturator (2), and is collected and analyzed.

The propargyl alcohol prepared by the process of the invention is the starting material for the preparation of pesticides and of 2-aminopyrimidine, which is used in pharmaceutical syntheses.

EXAMPLES

Examples 1-6

A cylindrical reactor having a diameter of 40 mm and a height of 2000 mm is filled with 1.5 l of catalyst, corresponding to a bed height of 1300 mm. The catalyst has an average particle size of 1.5 mm and contains 14% by weight of copper in the form of copper acetylide and 4% by weight of bismuth oxide, calculated as bismuth oxide, on silicon dioxide as the support material. The operating pressure is 3.3 bar. The reactor is flowed through from bottom to top with a formaldehyde solution which has been laden at a partial acetylene pressure of 3 bar and admixed with tetrahydrofuran according to Table 1. The feed of the use mixture is adjusted in such a way that the catalyst is kept fluidized. The pH of the feed solution is from 6 to 6.5. The expansion of the fluidized bed is 325 mm. The other reaction conditions can be taken from Table 1, the composition of the effluent, the space-time yields and the ratio of propynol to 1,4-butynediol in the effluent from Table 2.

Comparative Example 1

The comparative example is carried out like the inventive example, 1, except that the feed consists of 313 ml/h of a 30% by weight formaldehyde solution which has been laden at a partial acetylene pressure of 3 bar and is free of tetrahydrofuran. The further experimental conditions can be taken from Table 1 and the experimental results from Table 2.

TABLE 1

| Ex. No. | Temp. °C. | $FA^{1)}$ [% by wt.] | $FA^{1)}/THF^{2)}$ mixture [% by wt./% by wt.] | $FA^{1)}$ content in feed [% by wt.] | Feed [ml/h] |
|---|---|---|---|---|---|
| 1 | 80 | 30 | 1/1 | 15 | 321 |
| 2 | 75 | 30 | 1/1 | 15 | 313 |
| 3 | 75 | 30 | 2/1 | 20 | 317 |
| 4 | 80 | 30 | 1/0 | 30 | 347 |
| 5 | 80 | 49 | 1/1 | 25 | 311 |
| 6 | 75 | 49 | 1/1 | 25 | 318 |
| C1 | 80 | 30 | 1/0 | 30 | 313 |

$^{1)}$Formaldehyde
$^{2)}$Tetrahydrofuran

TABLE 2

| | Effluent | | | | | |
|---|---|---|---|---|---|---|
| | FA | | | | $STY^{3)}$ | Ratio |
| Ex. No. | [% by wt.] | Propynol [% by wt.] | 1,4-Butynediol [% by wt.] | Residue [% by wt.] | Propynol [kg/($I_{cat.}$*day)] | 1,4-Butynediol [kg/($I_{cat.}$*day)] | Propynol/1,4-Butynediol ratio [% by wt./% by wt.]] |
| 1 | 3.6 | 1.6 | 13.1 | 0.1 | 0.087 | 0.714 | 10.9/89.1 |
| 2 | 5 | 1.66 | 11.8 | 0.1 | 0.088 | 0.624 | 12.4/87.6 |
| 3 | 9 | 1.49 | 13.9 | 0.1 | 0.083 | 0.777 | 9.7/90.3 |
| 4 | 10.4 | 0.93 | 21.8 | 0.3 | 0.062 | 1.45 | 4.1/95.5 |
| 5 | 7.8 | 1.8 | 16.9 | 0.2 | 0.102 | 0.944 | 10.8/89.2 |
| 6 | 11.4 | 1.82 | 13.2 | 0.2 | 0.131 | 0.914 | 14.2/85.8 |
| C1 | 10.1 | 0.96 | 22.1 | 0.2 | 0.058 | 1.333 | 4.2/95.8 |

$^{3)}$Space-time yield

We claim:

1. A process for preparing propargyl alcohol, the process comprising:
   converting an aqueous formaldehyde solution comprising acetylene over a catalyst comprising copper acetylide at an operating pressure of from 1 to 15 bar and from 70 to 120° C. without forming a continuous gas phase, wherein the aqueous formaldehyde solution comprises tetrahydrofuran as the organic solvent for acetylene and the catalyst is arranged in a fluidized bed.

2. The process according to claim 1, wherein the expansion factor of the fluidized bed is ≦1.15.

3. The process of claim 1, wherein the operating pressure is from 3 to 7 bar.

4. The process of claim 1, wherein the pH of the aqueous formaldehyde solution is adjusted to from 3 to 8.

5. The process of claim 1, wherein the weight ratio of organic solvent to formaldehyde in the aqueous formaldehyde solution is from 0.1:1 to 20:1.

6. The process of claim 2, wherein the operating pressure is from 3 to 7 bar.

7. The process of claim 2, wherein the pH of the aqueous formaldehyde solution is adjusted to from 3 to 8.

8. The process of claim 2, wherein the weight ratio of organic solvent to formaldehyde in the aqueous formaldehyde solution is from 0.1:1 to 20:1.

* * * * *